(12) United States Patent
Choi (10) Patent No.: US 9,395,241 B1
(45) Date of Patent: Jul. 19, 2016

(54) SELF-ALIGNED SPECTROMETER

(71) Applicant: BBB INC., Seongnam-si, Gyeonggi-do (KR)

(72) Inventor: Jaekyu Choi, Seongnam-si (KR)

(73) Assignee: BBB INC., Seongnam-Si, Gyeonggi-Do (KR)

( * ) Notice: Subject to any disclaimer, the term of this patent is extended or adjusted under 35 U.S.C. 154(b) by 0 days.

(21) Appl. No.: 14/850,137

(22) Filed: Sep. 10, 2015

(30) Foreign Application Priority Data

Feb. 17, 2015 (KR) .......................... 10-2015-0024202

(51) Int. Cl.
*G01J 3/28* (2006.01)
*G01J 3/02* (2006.01)
*G01J 3/18* (2006.01)

(52) U.S. Cl.
CPC ................. *G01J 3/0208* (2013.01); *G01J 3/18* (2013.01); *G01J 3/2823* (2013.01)

(58) Field of Classification Search
CPC ............. G01J 3/02; G01J 3/0208; G01J 3/18; G01J 3/28; G01J 3/50; G01J 3/10
USPC ................................................... 356/300–445
See application file for complete search history.

(56) References Cited

U.S. PATENT DOCUMENTS 3,976,364 A  8/1976  Lindemann et al.
5,066,114 A * 11/1991  Hodges ............... G02B 3/12
                                                            359/665

FOREIGN PATENT DOCUMENTS

JP         2004354176 A      12/2004

* cited by examiner

*Primary Examiner* — Abdullahi Nur
(74) *Attorney, Agent, or Firm* — Hauptman Ham, LLP

(57) ABSTRACT

The present disclosure relates to a self-aligned spectrometer according to claim 1, comprising: a fixing device composed of light-transmittable materials, and which includes an air lens placed within the fixing device, and an optical waveguide of which at least a partial part is inserted and fixed in place within the fixing device through the first face of the fixing device.

12 Claims, 5 Drawing Sheets

SELF-ALIGNED SPECTROMETER

CROSS-REFERENCE TO RELATED APPLICATION

This application claims the priority of the Korean Patent Application No. 10-2015-0024202, filed on Feb. 17, 2015 in the Korean Intellectual Property Office (KIPO), and all the benefits accruing therefrom under 35 U.S.C. §119, the contents of which in their entirety are herein incorporated by reference.

TECHNICAL FIELD

The present invention relates to a self-aligned spectrometer, and more specifically, a self-aligned spectrometer that enables the alignment state of optical parts comprising the spectrometer to be maintained in a stable manner.

BACKGROUND ART

Spectrometer is a device used to quantify the type or concentration, and etc. of a specimen. A spectrometer, for example, includes a light source, a monochromator and an imaging sensor, and specifically, precise optical parts such as a light source, a prism, a grating, a mirror, a slit and an imaging sensor may be aligned according to a pre-defined order.

CITATION OF PRIOR ART

Patent Literature (Patent Literature 1) Registered Patent No. 10-0757017

DISCLOSURE OF INVENTION

Technical Problem

As aforementioned, since a spectrometer is composed of precise optical parts, the performance of a spectrometer may decline if the alignment state of optical parts is not maintained. The alignment state, for example, can become faulty if a strong impact is applied to a spectrometer, and if parts are not properly fixed in place due to defects caused from the designing process or the manufacturing process.

It is possible to design a spectrometer to enhance the fixture of optical parts or to protect a spectrometer from impacts in order to prevent the deformation of the alignment state, but this leads to an increase of manufacturing costs and thus, may deteriorate the price competitiveness of the product. Therefore, it is imperative to develop a measure to maintain the alignment state of optical parts in a stable manner, while controlling the increase of manufacturing costs.

The technical issue that the present invention is to resolve based on the technical problems mentioned above is to provide a self-aligned spectrometer that maintains the alignment state of optical parts through a fixing device that can be fabricated through a single manufacturing process with a homogeneous material.

Another technical issue that this present invention is to resolve is to provide a self-aligned spectrometer that can minimize the deformation of the alignment state of optical parts by fixing in place the position of optical parts such as an air lens, an optical waveguide, a spectral mirror and etc. through a fixing device.

The technical issues of the present invention are not limited to the above mentioned, but other issues not mentioned herein will be clearly understandable for those having ordinary skill in the art based upon the description which follows.

Effects of the Invention

While the present invention has effects that will be described more fully hereinafter, the effects of the present invention are not limited thereto.

First, as described above, the fixing device fabricated through a single manufacturing process using a homogeneous material, according to the present invention, may maintain the alignment state of optical parts, and thus, control the increase of a spectrometer's manufacturing costs and enable the miniaturization and integration of a spectrometer.

Second, it is possible to minimize the deformation of the alignment state of optical part since an air lens is included within the fixing device, an optical waveguide is inserted and fitted within the fixing device and a spectral mirror also is fixed via a fixing device.

DETAILED DESCRIPTION OF THE INVENTION

A desirable exemplary embodiment of the present invention will be described in detail hereinafter in reference with the accompanied drawings. The advantage and characteristic, and a method to achieve them will be obvious upon detailed description of the exemplary embodiments as well as accompanied drawings which follow. However, the present invention is not limited to the exemplary embodiments set forth herein, but can be embodied in many different forms. The exemplary embodiments are provided only to render the present disclosure complete and the scope of the present invention comprehensible to those having ordinary skill in the art. The present invention is only to be defined by the claims. A same reference mark used refers to a same element throughout the description.

Without separate definitions, all terms (including technical and scientific terms) used in the present description may be used for the meanings commonly understandable to those having ordinary skill in the art. In addition, the terms generally used and having definitions in dictionary, unless otherwise defined obviously in particular, should not be ideally or exaggeratedly interpreted.

The terms used in the present description are to explain the exemplary embodiments, not to limit the present invention thereto. In the present description, a singular form of word also includes a plural form thereof unless otherwise noted. The term "comprises" and/or "comprising" is not excluding the meaning that one or more elements other than the said element may exist or be added.

A self-aligned spectrometer according to embodiments of the present invention will be described more fully hereinafter with reference to the accompanying drawings, in which embodiments of the invention are shown.

Figure 1:
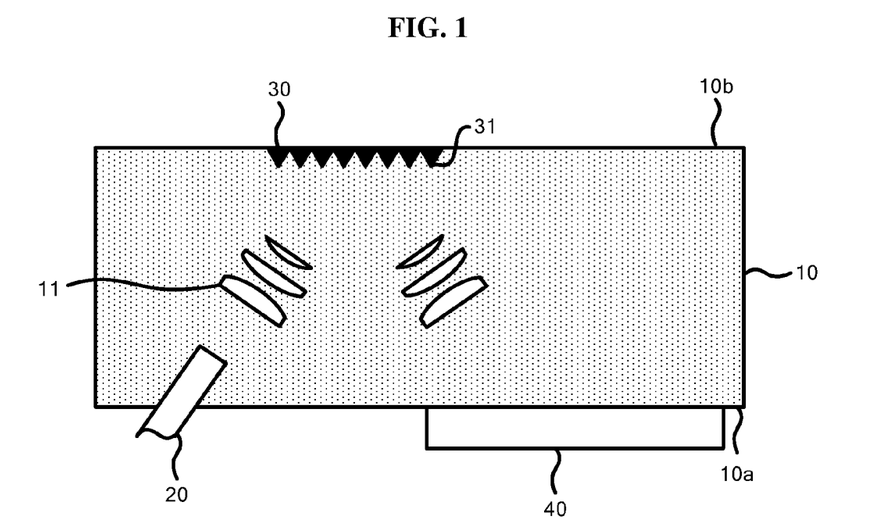
FIG. 1 is a diagram illustrating a rough composition of a self-aligned spectrometer according to the first exemplary embodiment of the present invention.
Figure 2:
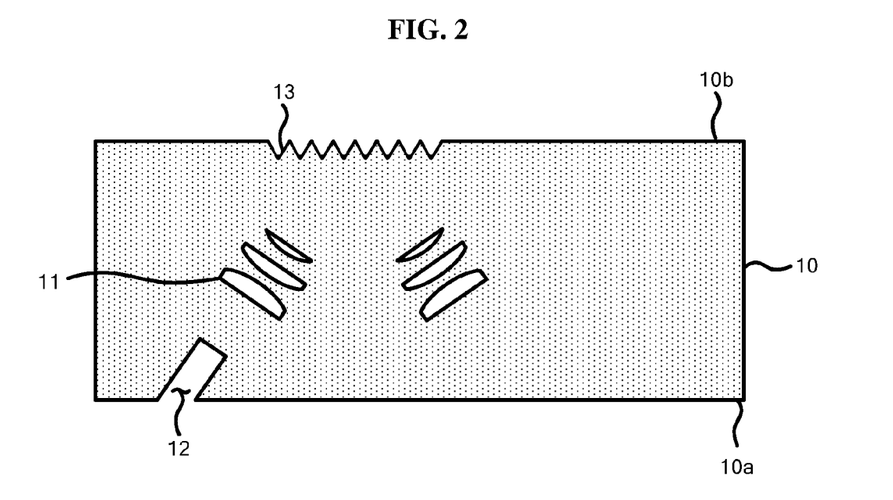
FIG. 2 is a diagram illustrating a rough composition of a fixing device included in the spectrometer of FIG. 1.

First, referring to FIG. 1 and FIG. 2, a self-aligned spectrometer according to the first exemplary embodiment of the present invention is described. Referring to FIG. 1, a diagram illustrating a rough composition of a self-aligned spectrometer according to the first exemplary embodiment of the present invention is disclosed, and referring to FIG. 2, a diagram illustrating a rough composition of a fixing device (10) included in the spectrometer of FIG. 1 is disclosed.

A self-aligned spectrometer according to the first exemplary embodiment of the present invention may be used to quantify the type or the concentration, and etc. of a sample. Specifically, the light, subject to measurement, which has passed through the sample or which has been reflected from the sample may be taken in by the spectrometer and be analyzed.

Specifically, a self-aligned spectrometer may include a fixing device (10), an optical waveguide (20), a spectral mirror (30), and an imaging sensor (40). Note that other exemplary embodiments of spectrometers that may implement one or more techniques described herein may include more components or fewer components than the components illustrated in FIG. 1.

A fixing device (10) is a fixing device (10) fabricated with light-transmittable materials, and may include an air lens (11) that is placed within the fixing device.

Since a fixing device (10) may be fabricated with materials that have excellent optical transparency, the light can be transmitted up to the imaging sensor by penetrating the fixing device (10). The material of the fixing device (10), for example, may comprise a photoresist with excellent optical transparency, but is not limited thereto. If the photoresist is used in the fixing device (10), it will be advantageous in mass producing spectrometers at a low cost.

A fixing device (10) can be fabricated by using a laser cured 3D printer, and the resolution of the 3D printer employed herein may be less than 1 sub-millimeter, but is not limited thereto. Specifically, referring to FIG. 2, the fixing device (10) may comprise multiple air lenses (11), a slit (12) and a diffraction grating pattern (13), and conduct patterning by using a photoresist as a material.

The inner part of a fixing device (10) can be employed with an air lens (11), and the air lens (11) employed herein may be an air-gap lens or an air-spaced lens. Furthermore, the air lens (11) may be filled with air and can be intentionally left as an empty space within the fixing device (10) to function as a lens. Specifically, the empty space in the inner part of the fixing device (10) can function as an air lens (11) due to the refractive index differences between the material of the fixing device (10) and the air filling the air lens (11).

There may be no limitation in the shape, number and sequence of an air lens (11), and an air lens with diverse shapes, numbers and sequences may be included in the inner part of a fixing device (10) according to the purpose. For example, at least a partial part of the air lens (11) may be placed within the fixing device (10) to induce the light to a spectral mirror (30), and other parts of the air lens (11) may be placed within a fixing device (10) to induce the light that is reflected from the spectral mirror (30) towards the imaging sensor (40), but is not limited thereto.

Meanwhile, a fixing device (10) may include a first face and a second face (10b) facing each other, and a slit (12) can be formed for an optical waveguide (20), discussed herein below, to be inserted and be fixed on the first face (10a) of the fixing device (10). The slit (12) may be extended to face the diffraction grating pattern (13) but is not limited thereto.

Furthermore, a diffraction grating pattern (13) may be formed on the second face (10b) of a fixing device (10), and the cross section of the diffraction grating pattern (13) may show a repetition of ripple-like patterns, but is not limited thereto. A spectral mirror (30), discussed herein below, may be disposed on the diffraction grating pattern (13) of the fixing device (10).

Therefore, a self-aligned spectrometer according to the exemplary embodiment of the present invention includes: an air lens (11) installed within the fixing device (10); a slit (12) made on the first face (10a) to insert and fix in place an optical waveguide (20); and a diffraction grating pattern (13) formed on the second face (10b) to install a spectral mirror (30). As such, the placement of optical parts comprising a spectrometer may be determined and fixed in place by a fixing device (10). That is, the deformation of the alignment state of optical parts can be minimized, since an air lens (11), an optical waveguide (20) and a spectral mirror (30) can be self-aligned and fixed in place in its respective positions through a fixing device (10).

An optical waveguide (20) may at least, be partially inserted and fixed in place within the fixing device (10) through the first face (10a) of a fixing device (10).

Specifically, an optical waveguide may be composed of a conduit, wherein an external light traversing a sample or which is reflected from a sample is transmitted to a fixing device (10). Since a slit (12), as aforementioned, is formed on first face (10a) of a fixing device (10), the alignment position of the optical waveguide (20) may be predetermined by the fixing device (10), and the optical waveguide (20) may be placed in a pre-defined position by inserting the optical waveguide (20) in the slit (12) of a fixing device (10).

Therefore, an optical waveguide (20), according to the first exemplary embodiment of the present invention, may be inserted and fixed in place according to the slit (12) of a fixing device (10) and thus, minimize the deformation of alignment state of the optical waveguide (20).

A spectral mirror (30) may disperse and reflect the incident light and may also function as a monochromator. That is, the spectral mirror (30) may reflect the incident light by dispersing the incident light. Referring to FIG. 1, the spectral mirror (30) may be disposed on the second face (10b) of a fixing device (10) facing the first face (10a) of a fixing device (10) to disperse and reflect the incident light that came from an optical waveguide (20) through an air lens (11).

Specifically, a spectral mirror (30) may be placed on a diffraction grating pattern (13) formed on the second face (10b) of a fixing device (10). The spectral mirror, for example, can be placed on the diffraction grating pattern (13) of a fixing device (10) via a metal deposition method. Therefore, the spectral mirror (30), placed by a metal deposition method, may include a diffraction grating pattern (31) that correspond to the shape of a diffraction grating pattern (13) of a fixing device (10), and specifically, a diffraction grating pattern (31)

of a spectral mirror (30) may be formed on the surface facing the first face (10a) of a fixing device (10).

Therefore, a spectral mirror (30) according to the exemplary embodiment of the present invention may disperse and reflect the incident light by using a diffraction grating pattern (31). That is, the spectral mirror (30) may reflect the incident light by dispersing the incident light. Furthermore, a spectral mirror (30) according to the first exemplary embodiment of the present invention can be placed via a metal deposition method on the diffraction grating pattern (13) of a fixing device (10). As such, the alignment state of the spectral mirror (30) may become more stable as the diffraction grating pattern (31) of a spectral mirror and the diffraction grating pattern (13) of a fixing device (10) can be placed in an interlocking manner.

Meanwhile, the spectral coverage of a spectrum can differ according to the type of metal used in a spectral mirror (30). If necessary, a spectral mirror (30) may comprise of various kinds of metal.

An imaging sensor (40) may detect an incident light and can be separated from an optical waveguide (20) and be placed on the first face (10a) of fixing device (10). An air lens (11), as aforementioned, may be placed between a spectral mirror (30) and an imaging sensor (40), and the air lens (11) may be place within a fixing device (10) to induce the dispersed and reflected light from the spectral mirror (30) to the imaging sensor (40).

As aforementioned, a spectrometer according to the first exemplary embodiment of the present invention can effectively maintain the alignment state of optical parts while reducing the manufacturing cost of the spectrometer, since the alignment state of optical parts can be maintained by using a fixing device (10) that can be fabricated through a single manufacturing process using a homogeneous material.

Figure 3:
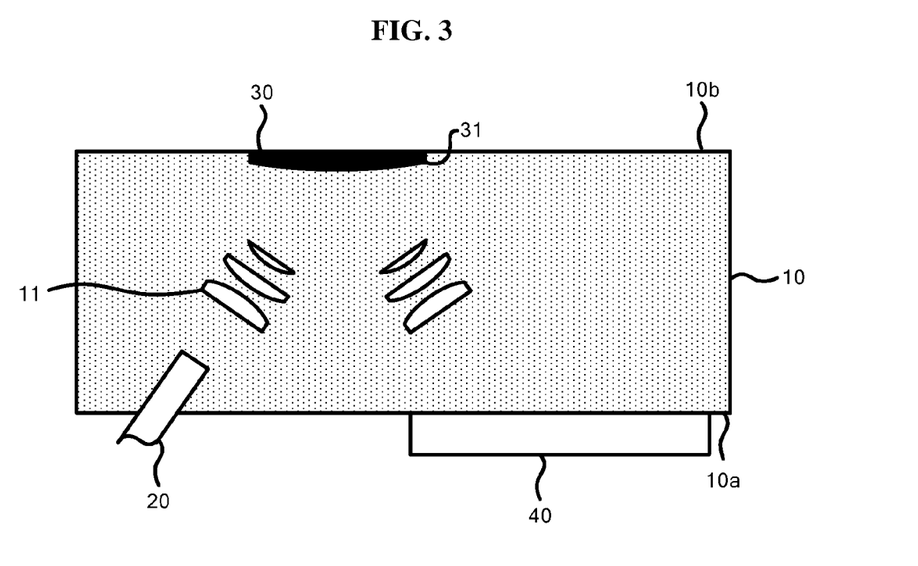
FIG. 3 is a diagram illustrating a rough composition of a self-aligned spectrometer according to the second exemplary embodiment of the present invention.

Hereinbelow, referring to FIG. 1 and FIG. 2, a self-aligned spectrometer according to the second exemplary embodiment of the present invention is described. Provided however, the following mainly describes differences from the spectrometer according to the first embodiment. Referring to FIG. 3, a diagram is disclosed illustrating a rough composition of a self-aligned spectrometer fabricated according to the second exemplary embodiment of the present invention, and referring to FIG. 4, a drawing is disclosed illustrating a rough composition of a fixing device (10) included in the spectrometer of FIG. 3.

Figure 4:
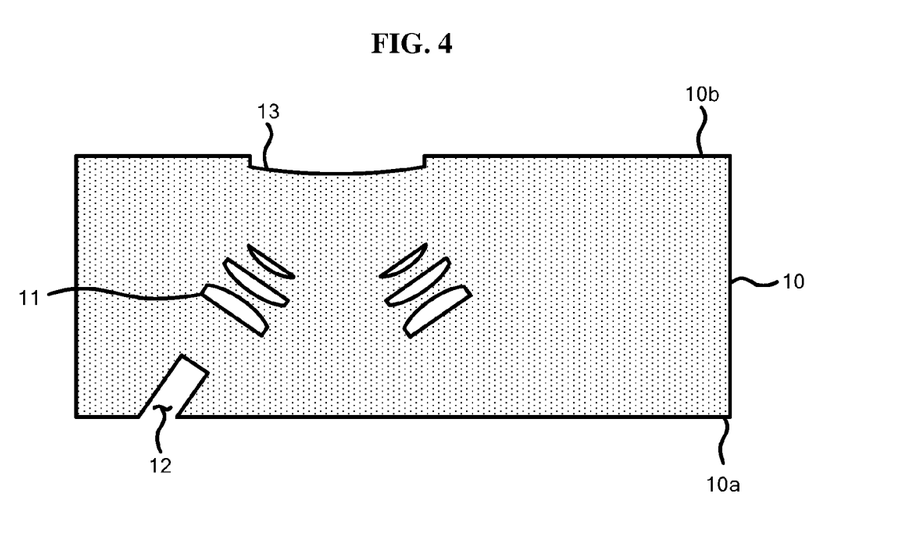
FIG. 4 is a diagram illustrating a rough composition of a fixing device included in the spectrometer of FIG. 3.

Referring to FIG. 3, the shape of a spectral mirror (30) of a self-aligned spectrometer according to the second exemplary embodiment of the present invention may differ from the self-aligned spectrometer according to the first exemplary embodiment of the present invention. Referring to FIG. 4, for example, the diffraction grating pattern (13) of a fixing device (10) may be curve-shaped and if necessary, a diffraction grating pattern (13) of a fixing device (10) can form a curvature as required. Furthermore, as a spectral mirror (30) can be placed on the diffraction grating pattern (13) of a fixing device (10) via a metal deposition method, the diffraction grating pattern (31) of a spectral mirror may also be curve-shaped corresponding to the diffraction grating pattern (13) of a fixing device (10).

Figure 5:
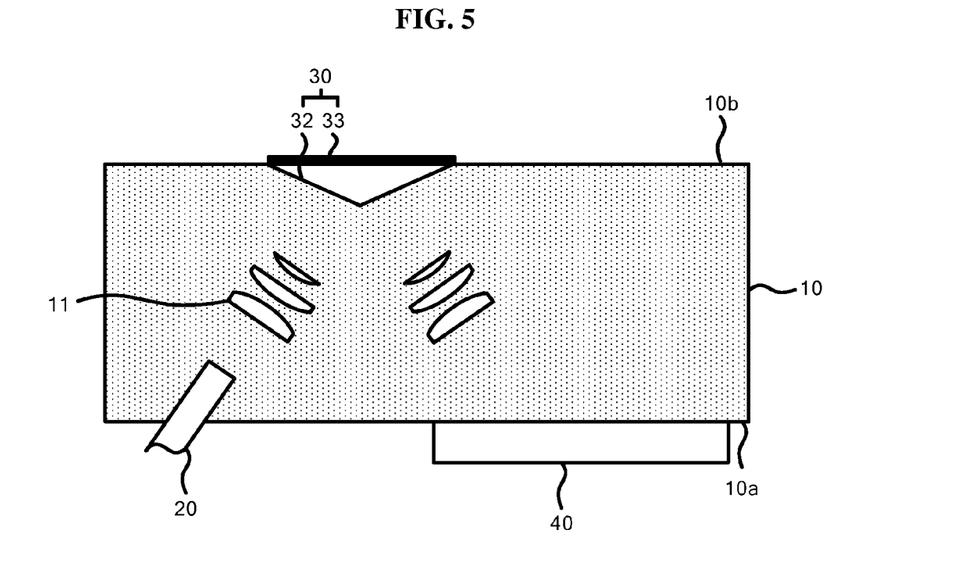
FIG. 5 is a diagram illustrating a rough composition of a self-aligned spectrometer according to the third exemplary embodiment of the present invention.
Figure 6:
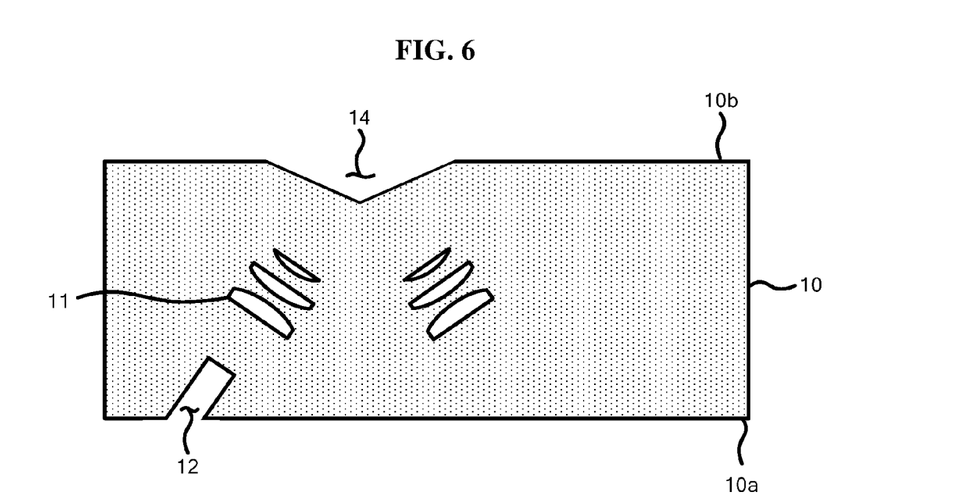
FIG. 6 is a diagram illustrating a rough composition of a fixing device included in the spectrometer of FIG. 5.

Hereinbelow, referring to FIG. 5 and FIG. 6, a self-aligned spectrometer according to the third exemplary embodiment of the present invention is described. Provided however, the following mainly describes differences from the spectrometer according to the first embodiment. Referring to FIG. 5, a diagram is disclosed illustrating a rough composition of a self-aligned spectrometer according to the third exemplary embodiment of the present invention, and referring to FIG. 6, a diagram is disclosed illustrating a rough composition of a fixing device (10) included in the spectrometer of FIG. 5.

Referring to FIG. 5, the components of a spectral mirror (30) of a self-aligned spectrometer according to the third exemplary embodiment of the present invention may differ from the self-aligned spectrometer according to the first exemplary embodiment of the present invention. Referring to FIG. 6, specifically, in a self-aligned spectrometer according to the present embodiment, a fixing device (10) may further include a groove (14) formed on the second face (10b). The groove (14) formed on the second face (10b) of the fixing device (10) herein, may be an area that can function as an air prism (32), that is, the cross-section of the groove (14) may be triangular-shaped to function as a prism, but is not limited thereto.

Again referring to FIG. 5 and FIG. 6, a spectral mirror (3) may include a reflecting mirror (33) formed on the second face (10b) to cover a groove (14) and an air prism (32) formed by the groove (14). Specifically, the groove (14) of a fixing device (10) may be covered by a reflecting mirror (33), and as such, an empty space surrounded by the second face (10b) of the fixing device (10) and the reflecting mirror (33) may be formed, wherein the empty space can function as an air prism (32). In particular, due to refractive index differences between the material of the fixing device (10) and the air filling the air prism (32), the groove (14) within the fixing device (10) can function as an air prism (32).

Figure 7:
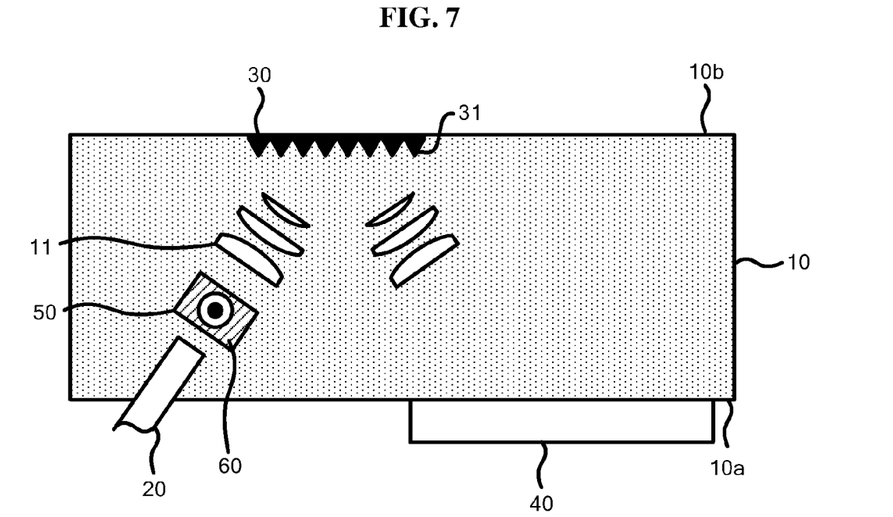
FIG. 7 and FIG. 8 are diagrams illustrating a rough composition of a self-aligned spectrometer according to the fourth exemplary embodiment of the present invention.
Figure 8:
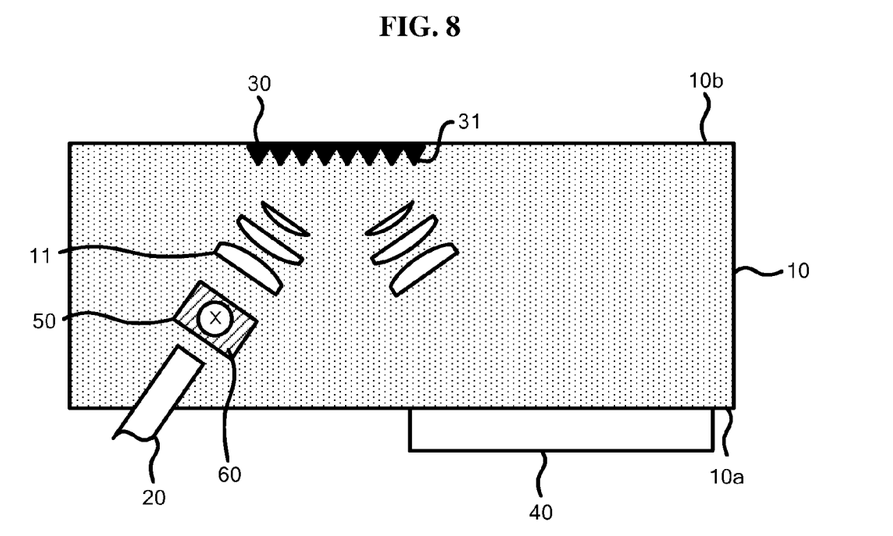

Hereinbelow, referring to FIG. 7 and FIG. 8, a self-aligned spectrometer according to the fourth exemplary embodiment of the present invention is described. Provided however, the following mainly describes differences from the spectrometer according to the first embodiment. Referring to FIG. 7 and FIG. 8, a diagram is disclosed illustrating a rough composition of a self-aligned spectrometer according to the fourth exemplary embodiment of the present invention.

Referring to FIG. 7, a self-aligned spectrometer fabricated according to the fourth exemplary embodiment of the present invention may further include a flow-cell (50) for the sample (60) to flow through, and the flow-cell (50) may be placed and fixed within a fixing device (10), and specifically, the flow cell (50) may be disposed between an optical waveguide (20) and an air lens (11).

That is, the sample is placed outside a fixing device (10) in a self-aligned spectrometer according to the first exemplary embodiment of the present invention, and the light emitted from the light source may pass through the sample in the outer part or be reflected from the external sample, then enter the spectrometer through an optical waveguide (20).

In contrast, in the self-aligned spectrometer fabricated according to the exemplary embodiment, an optical waveguide (20) may be directly connected to the light source and the light emitted from the light source can enter the spectrometer through the optical waveguide (20). Furthermore, the light emitted from the optical waveguide (20) traverses to the flow cell (50), wherein the sample (60) flows, and the incident light in the flow cell (50) may travel to the spectral mirror (30) by passing through or being reflected from the sample (60). That is, the light can pass through or can be reflected from the sample (60) within the fixing device (10) and the characteristics of the sample (60) can be analyzed by using such light.

Meanwhile, referring to FIG. 7, the direction of the sample (60) flow, in the diagram, may be of a direction heading and penetrating out of the surface, and referring to FIG. 8, the direction of the sample (60) flow, in the diagram, may be of a direction heading toward the surface.

Figure 9:
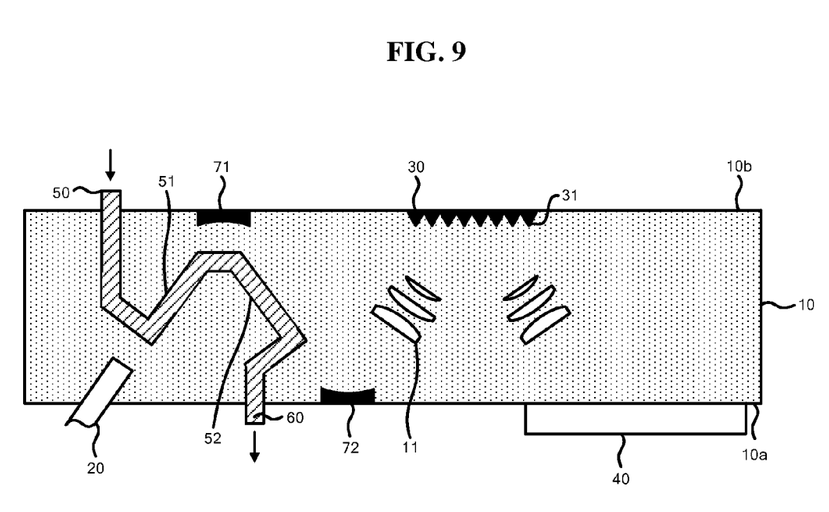
FIG. 9 is a diagram illustrating a rough composition of a self-aligned spectrometer according to the fifth exemplary embodiment of the present invention.

Hereinbelow, referring to FIG. 9, a self-aligned spectrometer according to the fifth exemplary embodiment of the present invention is described. Provided however, the following mainly describes differences from the spectrometer according to the fourth embodiment. Referring to FIG. 9, a diagram is disclosed illustrating a rough composition of a self-aligned spectrometer fabricated according to the fifth exemplary embodiment of the present invention.

Referring to FIG. 8, a self-aligned spectrometer according to the fifth exemplary embodiment of the present invention may have different shape of the flow-cell (50) from the self-aligned spectrometer according to the fourth exemplary embodiment of the present invention, and may further include a first focusing mirror and a second focusing mirror (71, 72).

Specifically, the flow-cell (50) enabling the sample (60) to flow through is placed and fixed in place within the fixing device (10), and may include a first base (51) extended to the first direction, and a second base (52) extended to the second direction that differs from the first direction. The sample (60), for example, may be injected through the flow-cell (50) on the second face (10b) of the fixing device (10), traverse along the first base (51) and the second base (52), and then be emitted through the flow cell (50) on the first face (10a) of the fixing device (10), but is not limited thereto.

Meanwhile the first base (51) of the flow-cell (50) may be placed between the optical waveguide (20) and the first focusing mirror (71), and the second base of the flow-cell (50) may be placed between the first focusing mirror (71) and the second focusing mirror (72). Furthermore, the first direction which is the extended direction of the first base (51) may face toward the first focusing mirror (71) from the optical waveguide (20), while the second direction which is the extended direction of the second base (52) may face toward the second focusing mirror (72) from the first focusing mirror (71), but is not limited thereto.

The first focusing mirror (71) may be placed on the second face (10b) of the fixing device (10) that faces the first face (10a), and may focus and reflect the incident light. That is, the first focusing mirror (71) may reflect the incident light by focusing the incident light. The first focusing mirror (71) may focus and reflect the light that passes through the sample (60) of the first base of the flow-cell (50) or is reflected from the corresponding sample (60).

The second focusing mirror (72) may be separated from the optical waveguide (20) and may be placed on the first face (10a) to focus and reflect the incident light. That is, the second focusing mirror (72) may reflect the incident light by focusing the incident light. The second focusing mirror (72) may focus and reflect he light that passes through the sample (60) of the second base of the flow-cell (50) or is reflected from the corresponding sample (60). Furthermore, the reflected light from the second focusing mirror (72) may traverse toward the air lens (11).

Meanwhile, the first focusing mirror (71) and the second focusing mirror (72) also may form a pattern in the fixing device (10) that correspond to the first focusing mirror (71) and the second focusing mirror (72), and may be formed via a metal deposition method on the corresponding pattern, but is not limited thereto.

According to a self-spectrometer according to the fifth exemplary embodiment of the present invention, the optical length may be extended by focusing the light passing through the sample (60) via the first and second focusing mirrors (71, 72), and the specification such as the sensitivity and the limit of detection can be significantly improved by Beer-Lambert's Law.

It is clearly understandable for those having ordinary skill in the art the present invention can be embodied in various forms, other than the exemplary embodiments set forth herein, without changes in its technical idea or essential characteristic. The exemplary embodiments described herein are only for the purpose of exemplifying the present invention in all aspects, not of limiting the scope of the present invention.

The invention claimed is:

1. A self-aligned spectrometer comprising:
a fixing device composed of light-transmittable materials, and which comprises an air lens placed within the fixing device;
an optical waveguide of which at least a partial part is inserted and fixed in place within the fixing device through the first face of the fixing device; and
a spectral mirror placed on the second face of the fixing device that faces the first face, and reflects the incident light by dispersing the incident light,
wherein the air lens composed of multiple air lenses, and at least a part of the air lens is placed within the fixing device to induce the light to the spectral mirror,
wherein the fixing device further comprises a groove formed on the second face, and the spectral mirror comprises a reflecting mirror placed on the second face to cover the groove and an air prism formed according to the groove.

2. A self-aligned spectrometer comprising:
a fixing device composed of light-transmittable materials, and which comprises an air lens placed within the fixing device;
an optical waveguide of which at least a partial part is inserted and fixed in place within the fixing device through the first face of the fixing device; and
a flow-cell, enabling a sample to flow through, that is placed and fixed in place within the fixing device,
wherein the flow-cell is placed between the optical waveguide and the air lens.

3. A self-aligned spectrometer comprising:
a fixing device composed of light-transmittable materials, and which comprises an air lens placed within the fixing device;
an optical waveguide of which at least a partial part is inserted and fixed in place within the fixing device through the first face of the fixing device;
a flow-cell, enabling a sample to flow through, that is placed and fixed in place within the fixing device and comprises a first base extended to a first direction and a second base extended to a second direction which is different from the first direction;
a first focusing mirror that is formed on the second face of the fixing device that faces the first face and reflects the incident light by focusing the incident light; and
a second focusing mirror separated from the optical waveguide, that is formed on the first face and reflects the incident light by focusing the incident light,
wherein the first base is placed between the optical waveguide and the first focusing mirror, and the second base is placed between the first focusing mirror and the second focusing mirror.

4. A self-aligned spectrometer according to claim 1, wherein the fixing device comprises a photoresist.

5. A self-aligned spectrometer according to claim 2, wherein the fixing device comprises a photoresist.

6. A self-aligned spectrometer according to claim 3, wherein the fixing device comprises a photoresist.

7. A self-aligned spectrometer according to claim 2, further comprising a spectral mirror placed on the second face of the fixing device that faces the first face,
  wherein the spectral mirror reflects the incident light by dispersing the incident light,
  wherein the air lens composed of multiple air lenses, and at least a part of the air lens is placed within the fixing device to induce the light to the spectral mirror.

8. A self-aligned spectrometer according to claim 3, further comprises a spectral mirror placed on the second face of the fixing device that faces the first face,
  wherein the spectral mirror reflects the incident light from the second focusing mirror by dispersing the incident light from the second focusing mirror,
  wherein the air lens composed of multiple air lenses, and at least a part of the air lens is placed within the fixing device to induce the light to the spectral mirror.

9. A self-aligned spectrometer according to claim 7, wherein the fixing device further comprises a diffraction grating pattern placed on the second face, and the spectral mirror is placed on the diffraction grating pattern.

10. A self-aligned spectrometer according to claim 8, wherein the fixing device further comprises a diffraction grating pattern placed on the second face, and the spectral mirror is placed on the diffraction grating pattern.

11. A self-aligned spectrometer structure according to claim 7, further comprising an imaging sensor separated from an optical waveguide and placed on the first face,
  wherein another part of the air lens is placed within the fixing device to induce the light that is reflected from the spectral mirror to the imaging sensor.

12. A self-aligned spectrometer structure according to claim 8, further comprising an imaging sensor separated from an optical waveguide and placed on the first face,
  wherein another part of the air lens is placed within the fixing device to induce the light that is reflected from the spectral mirror to the imaging sensor.

* * * * *